United States Patent
Gao et al.

(10) Patent No.: US 7,495,143 B2
(45) Date of Patent: Feb. 24, 2009

(54) HYDROCARBON CONVERSION USING NANOCRYSTALLINE ZEOLITE Y

(75) Inventors: Xingtao Gao, Edison, NJ (US); Johannes Hendrik Koegler, Montclair, NJ (US); Lawrence L. Murrell, South Plainfield, NJ (US); Philip J. Angevine, Woodbury, NJ (US)

(73) Assignee: Lummus Technology Inc., Bloomfield, NJ (US)

( * ) Notice: Subject to any disclaimer, the term of this patent is extended or adjusted under 35 U.S.C. 154(b) by 0 days.

(21) Appl. No.: 12/072,180

(22) Filed: Feb. 25, 2008

(65) Prior Publication Data

US 2008/0154083 A1 Jun. 26, 2008

Related U.S. Application Data

(63) Continuation of application No. 10/774,774, filed on Feb. 9, 2004, now Pat. No. 7,361,797, which is a continuation-in-part of application No. 10/067,719, filed on Feb. 5, 2002, now Pat. No. 6,793,911.

(51) Int. Cl.
*C07C 2/58* (2006.01)

(52) U.S. Cl. ..................................................... 585/722

(58) Field of Classification Search .................. 585/722
See application file for complete search history.

(56) References Cited

U.S. PATENT DOCUMENTS

| 3,549,557 A | * | 12/1970 | Pickert et al. ................. 502/73 |
| 3,851,004 A | | 11/1974 | Yang |
| 4,899,008 A | | 2/1990 | La Pierre et al. |
| 5,986,158 A | | 11/1999 | Van Broekhoven et al. |

OTHER PUBLICATIONS

E.H. van Broekhoven, "A New Solid Acid Isobutane Alkylation Technology AlkyClean", Catalyst Courier, Courier 45.

* cited by examiner

*Primary Examiner*—Thuan Dinh Dang
(74) *Attorney, Agent, or Firm*—Dilworth & Barrese, LLP.

(57) ABSTRACT

A process for alkylation of a hydrocarbon compound includes providing a catalyst including a zeolite Y having a crystal size of no more than 100 nm, and reacting an alkylatable hydrocarbon with an alkylating agent in the presence of the catalyst under alkylation reaction conditions to provide a gasoline product having a Research Octane Number of over 99.5.

17 Claims, No Drawings

HYDROCARBON CONVERSION USING NANOCRYSTALLINE ZEOLITE Y

CROSS-REFERENCE TO RELATED APPLICATIONS

The present application is a continuation of U.S. application Ser. No. 10/774,774 filed Feb. 9, 2004 and now issued as U.S. Pat. No. 7,361,797, which is a continuation-in-part of U.S. application Ser. No. 10/067,719 filed Feb 5, 2002 and now issued as U.S. Pat. No. 6,793,911, which is herein incorporated by reference, and to which priority is claimed.

BACKGROUND

1. Field of the Invention

The present invention is related to a method for conversion of hydrocarbon compounds, and particularly to the use of a zeolite catalyst for olefin/paraffin alkylation or aromatic alkylation.

2. Background of the Art

Alkylation pertains to the chemical addition of an alkyl group to another molecule to form a larger molecule. Commercial alkylation processes can typically be aromatic alkylation or olefin/paraffin alkylation. Aromatic alkylation typically involves the production of alkylaromatic compounds (e.g., ethylbenzene, cumene, etc.) by alkylating an aromatic compound (e.g., benzene) with an olefin (e.g., ethylene, propylene, etc.). Olefin/paraffin alkylation pertains to the reaction between a saturated hydrocarbon with an olefin to produce a highly branched saturated hydrocarbon with a higher molecular weight, for example, alkylation of isobutane with 2-butene to produce a gasoline product having a high octane number.

Unlike the production of gasoline by cracking high molecular weight petroleum fractions such as gas oil or petroleum residua, alkylation gives a cleaner gasoline product without sulfur or nitrogen impurities. Moreover, alkylate gasoline has little or no aromatic content, which is a further environmental benefit.

Various alkylation processes are known and used throughout the petroleum industry. For example, alkylation is routinely carried out commercially by using liquid acid catalysts such as sulfuric acid or hydrofluoric acid. Alternatively, solid zeolite catalysts have been used. Use of zeolites avoids the disadvantages of using highly corrosive and toxic liquid acids. However, zeolites can suffer from deactivation caused by coking. Various processes for alkylating hydrocarbons using zeolite-containing catalysts are disclosed in U.S. Pat. Nos. 3,549,557 and 3,815,004. An alkylation process using an acid solid catalyst using zeolitic or non-zeolitic material is disclosed in U.S. Pat. No. 5,986,158, which is herein incorporated by reference.

Zeolites are porous crystalline materials characterized by submicroscopic channels of a particular size and/or configuration. Zeolites are typically composed of aluminosilicate, but zeolite materials have been made in a wide range of other compositions. The latter are commonly referred to as microporous materials. The channels, or pores are ordered and, as such, provide unique properties, which make zeolites useful as catalysts or absorbents in industrial processes. For example, zeolites can be used for filtering out smaller molecules, which become entrapped in the pores of the zeolite. Also, zeolites can function as shape selective catalysts that favor certain chemical conversions within the pores in accordance with the shape or size of the molecular reactants or products. Zeolites have also been useful for ion exchange, such as for water softening and selective recovery of heavy metals.

Synthetic zeolites are traditionally made from sources of silica and aluminum (silica and alumina "nutrients") that react with each other, in the presence of materials that ensure highly alkaline conditions, such as water and $OH^-$. Other zeolites can be borosilicates, ferrosilicates, and the like. Many of the crystallization steps are conducted in the presence of an inorganic directing agent, or an organic template, which induces a specific zeolite structure that cannot easily be formed in the absence of the directing agent or template. Many of the organic templates are quaternary ammonium salts, but can also be linear amines, alcohols, and a variety of other compounds. As a hydroxide, some directing agents introduce hydroxyl ions into the reaction system; however, the alkalinity is usually dictated by the amount of sodium hydroxide (NaOH), potassium hydroxide (KOH), etc. The reaction typically involves a liquid gel phase in which rearrangements and transitions occur, such that a redistribution occurs between the alumina and silica nutrients, and molecular structures are formed which correspond to specific zeolites. Other metal oxides can also be included, such as titania-silica, boria-silica, etc. Some zeolites can only be made with organic templates. Other zeolites can only be made by means of an inorganic directing agent. Yet other zeolites can be made either by means of a hydrophilic (e.g., inorganic) directing agent or a hydrophobic (organic based) template.

Much of today's hydrocarbon processing technology is based on zeolite catalysts. Various zeolite catalysts are known in the art and possess well-arranged pore systems with uniform pore sizes. The term "medium pore" as applied to zeolites usually refers to zeolite structures having a pore size of 4-6 angstrom units (Å). "Large pore" zeolites include structures having a pore size of above 6 to about 12 Å. Since many hydrocarbon processing reactions at industrially relevant (i.e., high) conversion rates are limited by mass-transfer (specifically, intraparticle diffusion), a catalyst particle with an ideal pore structure will facilitate transport of the reactants to active catalyst sites within the particle and transport of the products out of the catalyst particle, but still achieve the desired shape selective catalysis. Zeolite morphology, i.e., crystal size, is another parameter in diffusion-limited reactions.

Catalysts have a limited life, for example, because of coking. Catalyst deactivation usually requires a reactor shutdown and catalyst regeneration. Although the use of two reactors operated in a "swing mode" (i.e., alternating use of reactors wherein one is operated for alkylation while the other is down for regeneration) allows for continuous production, it is nevertheless preferable to perform alkylation reactions with zeolite catalysts which have a long life so as to minimize the economic losses incurred by reactor shut down and catalyst regeneration.

SUMMARY

A process for alkylation of a hydrocarbon compound is provided herein. The process comprises providing a catalyst including a zeolite Y having a crystal size of no more than 100 nm; and reacting an alkylatable hydrocarbon with an alkylating agent in the presence of said catalyst under alkylation reaction conditions to provide an alkylate product.

The process described herein advantageously provides an alkylate product with a high Research Octane Number ("RON") as well as an alkylation reaction having a longer run time.

DETAILED DESCRIPTION OF PREFERRED EMBODIMENT(S)

The alkylation method described herein employs a zeolite with ultra-small, or nanocrystalline, crystal size, i.e., a crystal size of no more than about 100 nanometers ("nm"). The nanocrystalline zeolite possesses several advantages in connection with certain hydrocarbon conversion processes. For example, the effective diffusivity of many reactants and products is increased.

Secondly, the product selectivity is enhanced for certain processes, especially sequential reactions, where an intermediate product is desired. For example, ultra-small crystal size can reduce the amount of (1) over-cracking (e.g., the production of $C_3/C_4$ light gas products from the cracking of vacuum gas oil wherein distillate and naphtha products are the desired products) and (2) unwanted polyalkylation in aromatic alkylation processes. Also, coking, and the associated catalyst deactivation, is reduced for nanocrystalline zeolites by enabling the coke precursors to leave the catalyst before undergoing retrogressive condensation reactions.

Thirdly, the activity of the nanocrystalline zeolite catalyst is higher than for larger zeolite crystal catalysts, as diffusion limitation limits the accessibility of inner active sites in the latter case, resulting in a higher effective number of active sites per weight of catalyst for the nanocrystalline zeolite catalyst.

The method of the invention is described below in connection primarily with the use of zeolite Y as produced by the method described in commonly owned, copending U.S. application Ser. No. 10/067,719 for alkylation catalysis. Nanocrystalline zeolite Y produced in accordance with the method of application Ser. No. 10/067,719 has a cubic faujasite structure with an effective pore diameter of about 7 to 8 Å and a unit cell size of less than 25 Å. The zeolite Y as-synthesized also preferably has a silica to alumina mole ratio of less than about 10, often less than about 7. The crystal size of nanocrystalline zeolite Y is no more than about 100 nm, preferably no more than about 50 nm, and more preferably no more than about 25 nm.

While the synthesis of nanocrystalline zeolite Y can be carried out in the presence of an organic template, the preferred way, in terms of catalyst production costs, is the use of inorganic directing agents.

Nanocrystalline zeolite Y is useful in various hydrocarbon conversion processes, such as: aromatic alkylation and transalkylation in the production of ethylbenzene or cumene, alkylation of paraffins with olefins for the production of high octane gasoline, hydrocracking of vacuum gas oil to produce transportation fuels, hydroprocessing for making lube oil base stocks, preparation of linear alkylbenzenes or alkylnaphthalenes, selective hydrogenation, aromatic nitration, etc.

The method of preparing nanocrystalline zeolite Y includes impregnating a solid, porous silica-alumina particle or structure with a concentrated aqueous solution of an inorganic micropore-forming directing agent through incipient wetness impregnation. The porous silica-alumina material can be amorphous or crystalline. The amount of liquid is less than the amount of liquid that would cause surface gelation visible to the naked eye. The liquid provided to the solid, porous silica-alumina particle or structure is absorbed into and wets the interior voids of the latter, but does not form a paste-like material with the same. The liquid includes water, inorganic micropore-forming directing agent and also, if necessary, an organic template.

The organic template is selected in accordance with the desired product. Typical organic templates useful in zeolite synthesis include quaternary ammonium salts, linear amines and diamines, and alcohols. More specifically, particular organic templates include tetramethyl ammonium hydroxide or salts thereof, tetraethyl ammonium hydroxide or salts thereof, tetrapropyl ammonium hydroxide or salts thereof, pyrrolidine, hexane-1,6-diamine, hexane-1-6-diol, piperazine, and 18-crown-6 ethers.

The inorganic micropore-forming directing agent provides hydroxide ions and can be an alkali metal base or an alkaline earth metal base. However, with respect to the preparation of zeolite Y of the present invention, preferred micropore-forming directing agents are the inorganic alkali metal hydroxides, and preferably sodium hydroxide (NaOH). No organic templates are used. Since a high pH favors zeolite Y formation over other crystalline phases, as well as rapid nucleation and crystallization, high concentrations of the caustic directing agent are required. For example, when using concentration of 20% (by weight) or less of NaOH, other crystal phases such as cancrinite or zeolite P may be formed, no conversion might take place, too large zeolite Y crystals may be formed, or the conversion might take an unacceptably long period of time.

It has surprisingly been found that higher concentrations of inorganic directing agent significantly reduce the necessary reaction time. A preferred range of NaOH concentration in aqueous solution is 21% to about 60% by weight, more preferred is an NaOH concentration of 25% to about 60% by weight. Most preferred is an NaOH concentration of 45% to 50% by weight. Since higher NaOH concentrations result in exceedingly high viscosity and incomplete internal wetting, the intermediate concentration range represents an optimal level.

To maintain a "dry" material the amount of inorganic directing agent solution should not exceed 100% of the pore volume of the porous inorganic oxide material, and preferably ranges from about 80% to about 100% of the pore volume.

The degree of uniformity of the impregnation is important for successful crystallization of zeolite Y. Localized non-uniformity can result in non-zeolite Y by-product formation. To provide suitable mixing on a small scale (e.g., in the range of several grams to 100 grams) a mortar can be used to mix the silica-alumina with the solution of the micropore-forming directing agent. On a larger scale, a mixer in combination with a sprayer can be used.

The synthesis mixture of combined porous/amorphous silica-alumina and directing agent (NaOH) is then placed in a heating medium and heated to an elevated temperature of from about 50° C. to about 150° C., more preferably from about 70° C. to about 110° C. Uniform heating of the synthesis mixture is desired to preclude the formation of large zeolite crystals.

The synthesis mixture is maintained at the synthesis temperature for a time period sufficient to convert a sufficient amount of the silica-alumina to zeolite Y. The final framework structure after crystallization contains a substantial crystalline content (by weight), typically at least 15%, preferably at least 50% and most preferably from about 75% to 100% zeolite. The period of synthesis time can depend upon the synthesis temperature, lower synthesis temperatures requiring longer synthesis times. Synthesis time can range from 5 minutes to 150 hours, but more typically from 10 minutes to 48 hours, and preferably from about 15 minutes to about 30 hours.

After the required synthesis time, the synthesis mixture is preferably quenched by active cooling. Subsequently, the micropore-forming directing agent should be removed from the product to prevent further reaction in later treatment steps or during storage. Then, the sodium should be removed from the zeolite framework, e.g., by exchange with ammonium, using ion exchange techniques well known to those skilled in the art.

Optionally, the zeolite can be admixed with a matrix, binder, or catalyst support, material. Such materials include silica, alumina, aluminosilica, titania, zirconia and the like. Preferably the catalyst of the invention includes nanocrystalline zeolite Y and about 5% to 40% by weight of refractory oxide binder such as alumina, silica, silica-alumina, titania, zirconia, etc.

The ion-exchanged zeolite preferably has a sodium content of no more than about 0.2 wt %, more preferably no more than 0.1 wt %, and yet more preferably no more than about 0.05 wt %.

Nanocrystalline zeolite Y produced in accordance with the method of the invention has a mesopore to micropore volume ratio ranging from about 0.2 to about 6.0, a BET surface area of at least about 275 m$^2$/g and a unit cell size of from about 24.6 Å to about 24.9 Å.

Optionally, a catalytically active metal can be incorporated into the zeolite by, for example, ion-exchange or impregnation of the zeolite, or by incorporating the active metal in the synthesis materials from which the zeolite is prepared. The metal can be in a metallic form or combined with oxygen (e.g., metal oxide). Suitable catalytically active metals depend upon the particular process in which the catalyst is intended to be used and generally include, but are not limited to, Group VIII metals (e.g., Pt, Pd, Ir, Ru, Rh, Os, Fe, Co, Ni), rare earth "lanthanide" metals (e.g., La, Ce, Pr, etc.), Group IVB metals (e.g., Ti, Zr, Hf), Group VB metals (e.g., V, Nb, Ta), Group VIB metals (e.g., Cr, Mo, W), or Group IB metals (e.g., Cu, Ag, Au). In a preferred embodiment the catalytic metal is a rare earth metal, preferably lanthanum, or a mixture of rare earth metals having a high lanthanum content, with a rare earth metal to zeolite mass ratio of at least about 0.04, preferably at least about 0.08. Another catalytic metal is a noble metal, preferably platinum, with a metal to zeolite mass ratio of at least about 0.0001, preferably at least about 0.001.

In one embodiment, the method of the present invention employs nanocrystalline zeolite Y as a catalyst for olefin/paraffin alkylation. It has surprisingly been found that use of nanocrystalline zeolite Y having a crystal size of no more than 100 nm, preferably no more than 50 nm, and more preferably no more than 25 nm, results in longer catalyst life than conventional zeolite Y, and the resulting gasoline product has a higher RON, typically at least about 99.5.

The catalyst of the invention is particularly suited to be used for alkylating isoalkanes having 4-10 carbon atoms, such as isobutane, isopentane or isohexane or mixtures thereof, with olefins having 2-10 carbon atoms, preferably 2-6 carbon atoms, more preferably 3-5 carbon atoms. The alkylation of isobutane with butene or a mixture of butenes constitutes an attractive embodiment of the process according to the invention.

In another embodiment the catalyst of the invention can be used for the alkylation of an aromatic compound, such as benzene, with an olefin (e.g., ethylene, propylene, 1-butene, 2-butene, isobutene, etc.) to produce a corresponding alkylaromatic compound (e.g., ethylbenzene, cumene, di-isopropylbenzene, etc.). Also, the catalyst can be used for the transalkylation of polyalkylated aromatics with bare ring aromatics (e.g., benzene) to provide monoalkylated aromatics.

As will be evident to the skilled person, the process according to the invention can be applied in any suitable form, including fluidized bed processes, slurry processes and fixed bed processes. The process may be carried out in a number of beds, each with separate olefin addition. In such a case, the process of the invention may be carried out in each separate bed.

The olefin-paraffin alkylation process is practiced under conditions such that at least a portion of the alkylation agent and the alkylatable compound will be in the liquid phase or the supercritical phase. In general, the process according to the invention is practiced at a temperature in the range of about −40° C. to about 250° C., preferably in the range of about 50° C. to about 150° C., more preferably in the range of about 75° C. to about 95° C., and a pressure of from 1 to 100 bar, preferably of from 10 to 40 bar, more preferably of from 15 to 30 bar. The molar ratio of alkylatable compound to alkylation agent in the total feed in the reactor preferably is higher than 5:1, more preferably higher than 50:1. The feed rate (WHSV) of the alkylation agent generally is in the range of 0.01 to 5, preferably in the range of 0.05 to 0.5, more preferably in the range of 0.1 to 0.4 parts of alkylation agent per part of catalyst per hour. The WHSV of the alkylatable saturated hydrocarbon preferably is in the range of 0.1 to 500 hr$^{-1}$.

Another preferred process is aromatic alkylation such as the alkylation of benzene with ethylene to produce ethylbenzene or the alkylation of benzene with propylene to produce cumene, which may be carried out in a batch, semi-continuous or continuous fashion.

The examples below illustrate various features of the process of the present invention. The comparative examples do not exemplify the invention but are provided for the purpose of showing by comparison the surprising improvements achieved by the present invention over the use of conventional zeolite Y catalyst for olefin/paraffin alkylation, particularly, for the alkylation of isobutane with cis-2-butene to produce gasoline products. In all of the examples the olefin and paraffin were fed into a fixed bed reactor immersed in an oil bath to maintain a desired temperature. The reactor effluent was divided into two portions. One portion of the product was recycled back to the reactor as a recycle stream into which the olefin/paraffin feed was injected. Another portion, a product recovery stream, was sent to a condenser for separation of the alkylate product. Samples of the reactor effluent were drawn off for testing prior to separation of the product stream into a recycle stream and product recovery stream.

One test was performed for the determination of catalyst on-stream life by observation of the on-stream time which elapsed before "olefin breakthrough," i.e., the point at which 0.2% of the olefin leaves the reactor without being converted. The reactor effluent was monitored by chromatographic analysis to determine when olefin peaks appeared. The catalyst life is an important feature since the better the catalyst longevity is, the less the reactor needs to be taken off-line for catalyst regeneration.

Also, the total RON of the product was monitored. Each component of the product stream is characterized by a respective RON. The preferred alkylation products are trimethypentanes ("TMP's"), which have high research octane numbers (RON of about 100 to 110). The total RON of the alkylate product, which represents the anti-knock quality of the gasoline, was determined by calculating the weighted average of the RON's of the individual product components.

COMPARATIVE EXAMPLE 1

The zeolite catalyst evaluated in this Comparative Example was a commercially available zeolite HY and containing 70 wt. % zeolite HY in an alumina binder. The zeolite crystal size of this sample was 0.4-0.7 microns (i.e., 400-700 nm). The zeolite catalyst was derived from 1/32" extrudates and −18 to +25 mesh with a BET surface area of 562 m²/g. The test reactor was a recirculating differential fixed bed reactor in a system as described above with a feed containing isobutane and cis-2-butene in an isobutane/olefin (I/O) ratio of 15.9 and with a feed rate of 16.2 parts/hr. 4.6 Parts by weight of zeolite catalyst were charged to the reactor. The catalyst was pretreated in flowing nitrogen at 300° C. for 2 hours to remove moisture before the alkylation test was begun.

Alkylation was conducted at 400 psig and 80° C. with a recycle rate of 174 parts of the reaction effluent per parts of catalyst per hour. The test was carried out with samples taken every 45 minutes for GC analysis until olefin breakthrough. The catalyst life, as determined by olefin breakthrough, for this commercial zeolite Y catalyst was 2.7 hours. The RON as measured before olefin breakthrough was calculated to be 99.1. These results are summarized in Table 1.

COMPARATIVE EXAMPLE 2

The zeolite catalyst used in this Comparative Example is was 3.6 parts of commercially available zeolite HY and derived from 1/16" extrudates containing 80 wt % zeolite HY in an alumina binder. The zeolite crystal size of this sample was 0.4-0.7 microns. The dried catalyst was sieved to −18 to +25 mesh with a BET surface area of 556 m²/g. The pretreatment and alkylation reaction and conditions were conducted in the same manner as in Comparative Example 1. The results are set forth in Table 1.

COMPARATIVE EXAMPLE 3

The zeolite catalyst used in this Comparative Example was 3.6 parts by weight of a commercially available zeolite. HY derived from 1/16" extrudate containing 80 wt % zeolite HY in an alumina binder. The zeolite crystal size of this sample was 0.4-0.7 microns. The dried catalyst was sieved to −18 to +25 mesh with a BET surface area of 564 m²/g. The pretreatment and alkylation reaction and conditions were conducted in the same manner as in Comparative Example 1. The results are set forth in Table 1.

EXAMPLE 1

This example illustrates the invention. One part of porous silica-alumina with a silica/alumina ratio ("SAR") of 5.1 was impregnated with 1.05 parts of a solution containing 45 parts by weight of NaOH and 55 parts of distilled water. The impregnated material after aging was placed in an autoclave and heated at 85° C. for 24 hours. The material was then washed with distilled water and dried at 120° C. to obtain a product containing >95% zeolite Y crystals having sizes of from about 25 to 100 nm.

The nanocrystalline zeolite Y as synthesized was ion-exchanged with a mixture of $LaCl_3$ and $NH_4NO_3$ solution four times to remove sodium to below 0.2 wt %. After filtration and washing, the $LaNH_4Y$ sample was dried at 120° C. The dried powder was then mixed with appropriate amount of Nyacol alumina sol so that the final calcined product contained a zeolite concentration of about 80 wt %. The paste was dried at 90° C. for 1 hr and then calcined in accordance with the following program: 2° C./min to 120° C., held for 1 hr, 2° C./min to 500° C., held for 2 hr, 5° C./min cooling to room temperature.

The calcined pastes were ground and sieved to +20/−12 mesh size, of which 4.0 parts on the dry basis was loaded into the alkylation reactor for performance evaluation. The BET surface area of the final catalyst was 416 m²/g. The pretreatment and alkylation reaction conditions were the same as above. This sample had an olefin breakthrough of 6.2 hr and the alkylate had a RON of 100.2 before olefin breakthrough, as shown in Table 1.

EXAMPLE 2

The nanocrystalline zeolite Y as synthesized above in Example 1 was ion-exchanged to obtain $LaNH_4Y$ as above. The binding, pretreatment and test conditions were the same as in Example 1. The surface area of this sample was 409 m²/g. 4.0 Parts of the dried catalyst with a particle size of −18 to +25 mesh were charged to the reactor. The sample had an olefin breakthrough of 6.0 hours and the alkylate product had a RON of 100.3 before olefin breakthrough, as shown in Table 1.

EXAMPLE 3

The nanocrystalline zeolite Y as synthesized above in Example 1 was ion-exchanged to obtain $LaNH_4Y$ as above. The binding and pretreatment were the same as in Example 1. The surface area of this sample was 389 m²/g. The alkylation reaction conditions were the same as in Example 1 except that the feed rate was 21.3 parts/hr. 4.0 Parts of the dried catalyst with particle size of −18 to +25 mesh were charged to the reactor. The sample had an olefin breakthrough of 3.6 hours and the alkylate product had a RON of 100.4 before olefin breakthrough, as shown in Table 1.

EXAMPLE 4

The nanocrystalline zeolite Y as synthesized above in Example 1 was ion-exchanged to obtain $LaNH_4Y$ as above. The binding, pretreatment and test conditions were the same as in Example 1. The surface area of this sample was 413 m²/g. 4.0 Parts of the dried catalyst with particle size of −18 to +25 mesh were charged to the reactor. The sample had an olefin breakthrough of 8.0 hours and the alkylate product had a RON of 99.5 before olefin breakthrough, as shown in Table 1.

EXAMPLE 5

The nanocrystalline zeolite Y as synthesized above in Example 1 was ion-exchanged with a solution containing rare earth chlorides ("$RECL_3$") and ammonium nitrate ($NH_4NO_3$) several times to reduce the sodium content to below 0.2 wt % to obtain REY. The binding, pretreatment and test conditions were the same as in Example 1. The surface area of this sample was 396 m²/g. 3.6 Parts of the dried catalyst with particle size of −18 to +25 mesh were charged to the reactor. The sample had an olefin breakthrough of 3.4 hours and the alkylate product had a RON of 100.5 before olefin breakthrough, as shown in Table 1.

TABLE 1

| Example | Catalyst | Catalyst Life (hrs) | RON* | RON** |
|---|---|---|---|---|
| Comparative Example 1 | Commercial zeolite Y | 2.7 | 99.4 | 99.1 |
| Comparative Example 2 | Commercial zeolite Y | 5.7 | 101.0 | 98.1 |
| Comparative Example 3 | Commercial zeolite Y | 3.5 | 101.0 | 99.3 |
| Example 1 | Nanocrystalline zeolite Y | 6.2 | 102.5 | 100.2 |

TABLE 1-continued

| Example | Catalyst | Catalyst Life (hrs) | RON* | RON** |
|---|---|---|---|---|
| Example 2 | Nanocrystalline zeolite Y | 6.0 | 102.2 | 100.3 |
| Example 3 | Nanocrystalline zeolite Y | 3.6 | 101.8 | 100.4 |
| Example 4 | Nanocrystalline zeolite Y | 8.0 | 102.3 | 99.5 |
| Example 5 | Nanocrystalline zeolite Y | 3.4 | 102.0 | 100.5 |

*After 1 hour of reaction
**Before olefin breakthrough

The test results show the unexpected superiority of the nanocrystalline catalyst of the present invention. For example, the average catalyst life of Comparative Examples 1 to 3 (conventional zeolite Y) at an average WHSV of about 0.25 parts of olefin per part of catalyst per hour was 3.9 hours with an average RON before olefin breakthrough of about 98.8. The average catalyst life of Examples 1 to 5 (nanocrystalline zeolite Y) at an average WHSV of about 0.26 parts of olefin per part of catalyst per hour was 5.36 hours with a corresponding average RON before olefin breakthrough of about 100.2.

While the above description contains many specifics, these specifics should not be construed as limitations on the scope of the invention, but merely as exemplifications of preferred embodiments thereof. Those skilled in the art will envision many other possibilities within the scope and spirit of the invention as defined by the claims appended hereto.

What is claimed is:

1. A process for alkylation of a hydrocarbon compound comprising.
   a) providing a catalyst including a zeolite Y having a crystal size of no more than 100 nm;
   b) reacting an alkylatable hydrocarbon with an alkylating agent in the presence of said catalyst under alkylation reaction conditions to provide an alkylate product, wherein the alkylatable hydrocarbon is paraffin and the alkylating agent is olefin.

2. The process of claim 1 wherein the alcylatable hydrocarbon is isobutane and the alkylating agent is a butene.

3. The process of claim 2 wherein the alkylate product comprises a gasoline having a research octane number of at least 99.5.

4. The process of claim 1 wherein the step of providing the catalyst comprises:
   a) providing a porous inorganic oxide
   b) impregnating the porous inorganic oxide with a liquid solution containing an inorganic micropore forming directing agent which provides hydroxide ions, wherein the amount of liquid solution is no more than about 100% of the pore volume of the inorganic oxide, and the concentration of the micropore forming directing agent in the liquid solution ranges from about 25% to about 60% by weight, and
   c) heating the impregnated porous inorganic oxide at an elevated synthesis temperature for a duration of time sufficient to form a zeolite containing product.

5. The process of claim 4 wherein the liquid solution of inorganic micropore forming directing agent is an aqueous solution of sodium hydroxide.

6. The process of claim 1 wherein the zeolite Y has a crystal size of no more than about 50 nm.

7. The process of claim 1 wherein the zeolite Y has a crystal size of no more than about 25 nm.

8. The process of claim 1 wherein the zeolite Y has a sodium content of no more than about 0.2 wt%.

9. The process of claim 1 wherein the zeolite Y has a sodium content of no more than about 0.1 wt%.

10. The process of claim 1 wherein the zeolite Y has a sodium content of no more than about 0.05 wt%.

11. The process of claim 1 wherein the catalyst includes a refractory oxide binder.

12. The process of claim 11 wherein the refractory oxide binder comprises one or more oxides selected from the group consisting of silica, alumina, silica-alumina, titania and zirconia.

13. The process of claim 1 wherein the zeolite Y includes one or more metals selected from the group consisting of Pt, Pd, Ir, Ru, Rh, Os, Fe, Co, Ni, La, Ce, Pr, Ti, Zr, Hf, V, Nb, Ta, Cr, Mo, W, Cu, Ag and Au.

14. The process of claim 1 wherein the zeolite Y includes lanthanum and wherein the lanthanum to zeolite mass ratio is at least about 0.04.

15. The process of claim 1 wherein the zeolite Y has a mesopore to micropore volume ratio of from about 0.2 to about 0.6.

16. The process of claim 1 wherein the catalyst has a BET surface area of at least about 275 $m^2/g$, and wherein the zeolite Y has a rare earth metal component with a mass ratio of rare earth metal to zeolite of at least about 0.04, wherein the zeolite has a mesopore to micropore volume ratio of from about 0.2 to about 6.0, and a unit cell size of from about 24.6 Å to about 24.9 Å.

17. The process of claim 1 wherein the alkylation reaction conditions include a temperature of from about −40° C. to about 250° C., a pressure of from about 1 bar to 100 bar, and a WHSV of from about 0.1 to about 500 $hr^{-1}$.

* * * * *